United States Patent [19]

Hunkeler et al.

[11] 4,352,818
[45] Oct. 5, 1982

[54] DIAZEPINE DERIVATIVES AND THEIR USE

[75] Inventors: Walter Hunkeler, Magden; Emilio Kyburz, Reinach, both of Switzerland

[73] Assignee: Hoffmann-La Roche Inc., Nutley, N.J.

[21] Appl. No.: 349,879

[22] Filed: Feb. 18, 1982

[30] Foreign Application Priority Data

Feb. 27, 1981 [CH] Switzerland .................... 1341/81

[51] Int. Cl.³ ............... A61K 31/55; C07D 487/04; C07D 513/14
[52] U.S. Cl. .................... 424/273 R; 260/239.3 T; 260/239.3 B; 260/239.3 P
[58] Field of Search .................. 260/239.3 T, 239.3 P; 424/273 R

[56] References Cited

U.S. PATENT DOCUMENTS 4,316,832  2/1982  Gerecke et al. ............ 260/239.3 T Primary Examiner—Robert T. Bond
Attorney, Agent, or Firm—Jon S. Saxe; Bernard S. Leon; Frank P. Hoffman

[57] ABSTRACT

There is presented imidazodiazepines of the formula

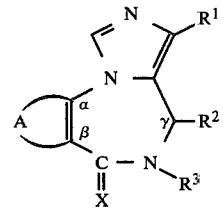

I wherein A together with the two carbon atoms denoted as α and β is the group

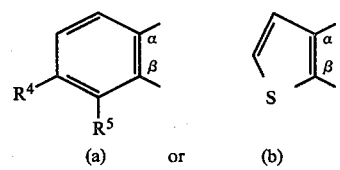

(a) or (b)

$R^1$ is hydrogen, lower alkyl, lower alkoxymethyl, halogen or nitro, $R^4$ is hydrogen, trifluoromethyl or halogen, $R^5$ is hydrogen, fluoromethyl, halogen or lower alkyl and X is an oxygen or sulphur atom, and either $R^2$ is hydrogen and $R^3$ is lower alkyl or $R^2$ and $R^3$ together are trimethylene or propenylene and the carbon atom denoted as γ has the (S)— or (R,S)— configuration, and their pharmaceutically acceptable acid addition salts. The compounds antagonize the central-depressant, muscle relaxant, ataxic, blood pressure-lowering and respiratory-depressant properties of 1,4-benzodiazepines which have tranquillizing activity. Thus they can be used, for example, as antidotes in the case of intoxications with 1,4-benzodiazepines which have tranquillizing activity.

Also presented are various methods to produce the imidazodiazepine derivatives.

12 Claims, No Drawings

DIAZEPINE DERIVATIVES AND THEIR USE

DESCRIPTION OF THE INVENTION

The present invention is concerned with imidazodiazepines. In particular, the invention is concerned with imidazodiazepines of the formula

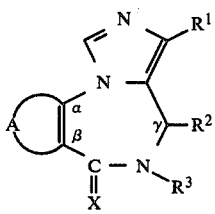

wherein A together with the two carbon atoms denoted as $\alpha$ and $\beta$ is the group

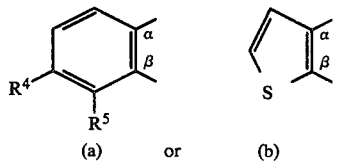

(a)  or  (b)

$R^1$ is hydrogen, lower alkyl, lower alkoxymethyl, halogen or nitro, $R^4$ is hydrogen, trifluoromethyl or halogen, $R^5$ is hydrogen, trifluoromethyl, halogen or lower alkyl and X is an oxygen or sulfur atom, and either $R^2$ is hydrogen and $R^3$ is lower alkyl or $R^2$ and $R^3$ together are trimethylene or propenylene and the carbon atom denoted as $\gamma$ has the (S)— or (R,S)— configuration, and pharmaceutically acceptable acid addition salts thereof.

These compounds are novel and possess valuable pharmacodynamic properties; they can be used in the control or prevention of illnesses.

Objects of the present invention are compounds of formula I and pharmaceutically acceptable acid addition salts thereof per se and as pharmaceutically active substances, the manufacture of these compounds and intermediates for the manufacture of these compounds, medicaments containing a compound of formula I or a pharmaceutically acceptable acid addition salt thereof and the manufacture of such medicaments.

The term "lower alkyl" denotes saturated hydrocarbon residues, which can be straight-chain or branched-chain, containing at most 7, preferably at most 4, carbon atoms such as methyl, ethyl, n-propyl, isopropyl, n-butyl, s-butyl, t-butyl and the like. The term "lower alkoxymethyl" includes groups such as methoxymethyl, ethoxymethyl and the like. The term "halogen" signifies fluorine, chlorine, bromine and iodine.

$R^1$ preferably is hydrogen, methyl, methoxymethyl, halogen or nitro. When $R^2$ is hydrogen, then $R^3$ preferably is methyl. When $R^2$ and $R^3$ together are trimethylene, then the carbon atom denoted as $\gamma$ in formula I has the (S)-configuration.

If the symbol A is group (a) hereinbefore, then $R^4$ preferably is hydrogen, chlorine or fluorine and $R^5$ preferably is hydrogen or chlorine, whereby preferably at least one of $R^4$ and $R^5$ is hydrogen.

Compounds of formula I which are especially preferred are:

3,7-Dichloro-4,5-dihydro-5-methyl-6H-imidazo[1,5-a][1,4]benzodiazepin-6-one,
(R,S)-1,8-dichloro-11,13a-dihydro-9H-imidazo[1,5-a]pyrrolo[2,1-c][1,4]benzodiazepin-9-one,
3-chloro-4,5-dihydro-5-methyl-6H-imidazo[1,5-a][1,4]-benzodiazepin-6-one and
7-chloro-4,5-dihydro-3-(methoxymethyl)-5-methyl-6H-imidazo[1,5-a][1,4]benzodiazepin-6-one.

Other compounds of formula I which are preferred are:

(S)-1-Chloro-10,11,12,12a-tetrahydro-8H-imidazo[5,1-c]pyrrolo[1,2-a]thieno[3,2-e][1,4]diazepin-8-one,
3-chloro-8-fluoro-4,5-dihydro-5-methyl-6H-imidazo[1,5-a][1,4]benzodiazepin-6-one,
4,5-dihydro-3-(methoxymethyl)-5-methyl-6H-imidazo[1,5-a][1,4]benzodiazepin-6-one,
4,5-dihydro-3-iodo-5-methyl-6H-imidazo[1,5-a][1,4]benzodiazepin-6-one,
4,5-dihydro-5-methyl-3-nitro-6H-imidazo[1,5-a][1,4]benzodiazepin-6-one,
3-bromo-4,5-dihydro-5-methyl-6H-imidazo[1,5-a][1,4]benzodiazepin-6-one,
7-chloro-4,5-dihydro-5-methyl-6H-imidazo[1,5-a][1,4]benzodiazepin-6-one,
3-bromo-8-fluoro-4,5-dihydro-5-methyl-6H-imidazo[1,5-a][1,4]benzodiazepin-6-one,
3-chloro-4,5-dihydro-5-methyl-6H-imidazo[1,5-a][1,4]benzodiazepine-6-thione,
(S)-1-chloro-11,12,13,13a-tetrahydro-9H-imidazo[1,5-a]pyrrolo[2,1-c][1,4]benzodiazepin-9-one,
(S)-1-bromo-11,12,13,13a-tetrahydro-9H-imidazo[1,5-a]pyrrolo[2,1-c][1,4]benzodiazepin-9-one and
(R,S)-8-chloro-11,13a-dihydro-9H-imidazo[1,5-a]pyrrolo[2,1-c][1,4]benzodiazepin-9-one.

The imidazodiazepines of formula I and their pharmaceutically acceptable acid addition salts can be manufactured in accordance with the invention by (a) decarboxylating a compound of the formula

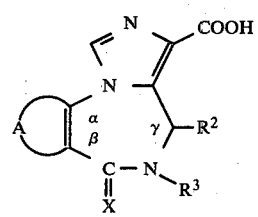

wherein A, X, $R^2$ and $R^3$ are as above or (b) halogenating a compound of the formula

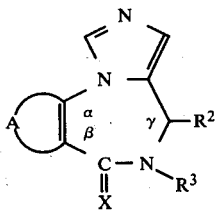
Ia wherein A, X, $R^2$ and $R^3$ are as above, in the imidazole ring, or (c) replacing the amino group in a compound of the formula

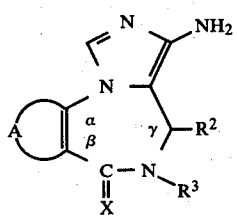
III wherein A, X, $R^2$ and $R^3$ are as above, by a nitro group or by a halogen atom, or (d) oxidizing the amino group in an amino compound of formula III above to the nitro group, or (e) etherifying a compound of the formula

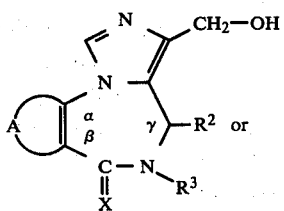
X

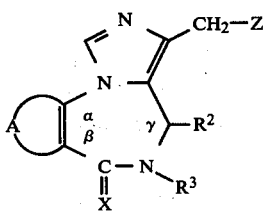
IVa wherein A, X, $R^2$ and $R^3$ are as above and Z is a leaving group, with an alkylating agent yielding a lower alkyl group in the case of a compound of formula X or with a lower alcohol in the case of a compound of formula IVa, or (f) cleaving off under reductive conditions the leaving group denoted by Z in a compound of the formula

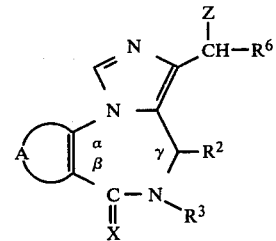
IV wherein A, X, Z, $R^2$ and $R^3$ are as above and $R^6$ is hydrogen or lower alkyl, or (g) converting the carbonyl group in a compound of the formula

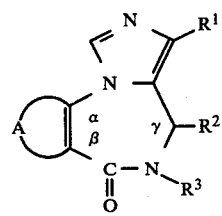
Ib wherein A, $R^1$, $R^2$ and $R^3$ are as above, into the thiocarbonyl group, and (h) if desired, converting a compound of formula I obtained into a pharmaceutically acceptable acid addition salt.

In accordance with process variant (a), compounds of formula I in which $R^1$ is hydrogen can be manufactured by decarboxylating carboxylic acids of formula II. This decarboxylation is conveniently carried out by dry heating the carboxylic acid of formula II, which may be crude, to temperatures of about 150° C. to about 400° C., the temperature depending on the melting point of the particular compound of formula II used.

In accordance with process variant (b), compounds of formula I in which $R^1$ is halogen can be manufactured by halogenating compounds of formula Ia. Suitable halogenating agents are, for example, N-chlorosuccinimide, N-bromosuccinimide, N-chloroacetamide, N-bromoacetamide and elemental iodine. As solvents there are conveniently used inert organic solvents, for example halogenated hydrocarbons such as methylene chloride, 1,2-dichloroethane, chloroform and the like, dimethylformamide, dimethylacetamide, acetonitrile, ethers such as diethyl ether, tetrahydrofuran, dioxan and the like, etc. The halogenation can be carried out in a temperature range of about 0° C. to the boiling point of the mixture, a range of about room temperature to about 100° C. being preferred.

In accordance with process variant (c), compounds of formula I in which $R^1$ is halogen or nitro can be manufactured by replacing the amino group in a compound of formula III by a halogen atom or by the nitro group. Conveniently, the amono compound of formula III is converted into a corresponding diazonium salt and this is reacted, optionally without previous isolation, with a nitrite such as sodium nitrite or with a halide (e.g. with a chloride or bromide) in the presence of a copper (I) salt. The presence of a copper (I) salt is not necessary for the manufacture of the corresponding iodides. Corresponding fluorides are conveniently manufactured via a corresponding diazonium tetrafluoroborate, for example by irradiation with UV-light. These reactions are carried out in aqueous solutions at temperatures of about −10° C. to about room temperature.

In accordance with process variant (d), compounds of formula I in which $R^1$ is nitro can also be manufactured by oxidizing an amino compound of formula III. Suitable oxidizing agents are, for example, peracids such as peracetic acid, trifluoroperacetic acid, m-chloroperbenzoic acid and perbenzoic acid, and the like. As solvents there come into consideration, depending on the oxidizing agent used, carboxylic acids such as acetic acid etc, halogenated hydrocarbons such as methylene chloride, chloroform, 1,2-dichloroethane etc, or the like. As a rule, the oxidation is carried out at a temperature of about 0° C. to about room temperature.

In accordance with process variant (e), compounds of formula I in which $R^1$ is lower alkoxymethyl can be manufactured by etherifying an alcohol of formula X with an alkylating agent yielding a lower alkyl group or etherifying a compound of formula IVa with a lower alcohol. This etherification is carried out in an inert organic solvent such as dimethylformamide, hexamethylphosphoric acid triamide, dimethyl sulphoxide, tetrahydrofuran or any other suitable organic solvent and in the presence of a base which is sufficiently strongly basic to form the corresponding alcoholate from the alcohol of formula X or from the lower alcohol. Suitable bases are, for example, alkali metal hydrides such as sodium hydride, alakli metals such as sodium and alkali metal amides such as lithium amide and lithium diisopropylamide. Suitable alkylating agents are, for example, alkyl halides such as methyl iodide, ethyl iodide and ethyl bromide and dialkyl sulphates such as dimethyl sulphate and diethyl sulphate. This etherification is conveniently carried out at a temperature between about 0° C. and about 50° C.

In accordance with process variant (f), compounds of formula I in which $R^1$ is lower alkyl can be manufactured by cleaving off under reductive conditions the leaving group denoted by Z in a compound of formula IV. This process variant is carried out according to methods known per se, the choice of the suitable leaving group denoted by Z as well as the determination of the conditions suitable for the cleavage, under which other structural elements present in the molecule should not be affected, presenting no difficulties to a person skilled in the art. Especially suitable leaving groups for the present process variant are, for example, halogen atoms such as chlorine, bromine and iodine which can be cleaved off readily under hydrogenolytic conditions, for example by treatment with elemental hydrogen in the presence of a suitable catalyst (e.g. palladium/carbon, Raney-nickel etc) in an inert organic solvent. Suitable solvents are, for example, alcohols such as methanol, ethanol and isopropanol, ethers such as diethyl ether, tetrahydrofuran, dioxan and dimethoxyethane, and the like. Depending on the reactivity of the catalyst used, the cleavage is carried out at pressures of about normal pressure up to about 300 bar and at temperatures of about room temperature up to about 150° C.

In accordance with process variant (g), compounds of formula Ib can be converted into corresponding compounds of formula I in which X is a sulphur atom by treatment with a sulphurizing agent, which can be carried out in a manner known per se. For example, the sulphurizing agent can be phosphorus pentasulphide, this being preferably used in excess and the reaction being advantageously carried out in an inert organic solvent such as dioxan, methylene chloride or the like in the presence of triethylamine at a temperature of about 50° C. up to the reflux temperature of the reaction mixture. Other suitable sulphurizing agents are compounds such as 2,4-bis(p-methoxyphenyl)-1,3,2,4-dithiaphosphetane-2,4-disulphide; such sulphurizing agents being used in approximately the calculated amount and the reaction being carried out in the presence of an inert solvent such as, for example, toluene or xylene, conveniently at the reflux temperature of the reaction mixture, or in hexamethylphosphoric acid triamide at a temperature between about 60° and 110° C.

In accordance with process variant (h), compounds of formula I can be converted into pharmaceutically acceptable acid addition salts. The manufacture of such pharmaceutically acceptable acid addition salts is carried out according to generally usual methods. The salts provided by the present invention are salts formed with inorganic acids and organic acids; for example, hydrochlorides, hydrobromides, sulphates, methanesulphonates, p-toluenesulphonates, oxalates and the like.

The compounds of formula II used as starting materials can be prepared starting from compounds of the formula

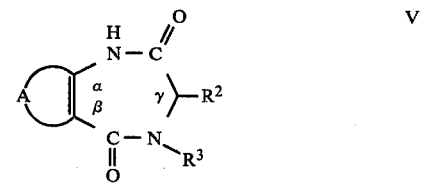

wherein A, $R^2$ and $R^3$ are as above according to Formula Scheme 1 hereinafter in which A, $R^2$ and $R^3$ are as above, Y is a leaving group and $R^7$ is lower alkyl:

Formula Scheme 1

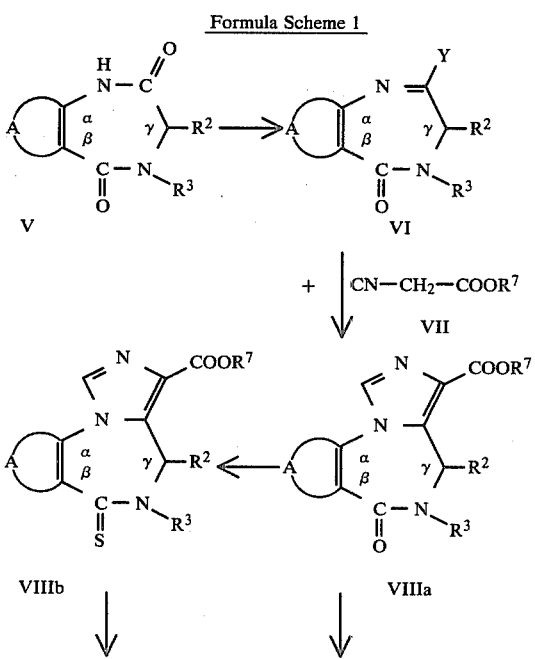

-continued
Formula Scheme 1

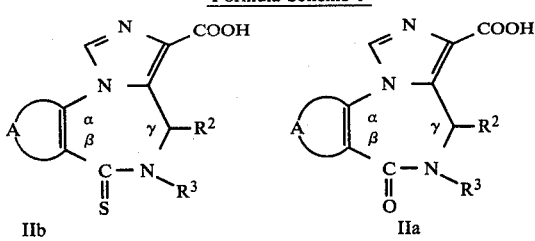

The leaving group denoted by Y in formula VI is, for example, a readily cleavable phosphinyl group, e.g. a group of the formula

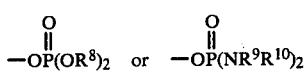

wherein $R^8$ is lower alkyl and $R^9$ and $R^{10}$ each are lower alkyl, allyl, phenyl or substituted phenyl or $R^9$ and $R^{10}$ together with the nitrogen atom is an unsubstituted or substituted heterocyclic ring with 3 to 8 members (such as morpholine), a halogen atom, an alkylthio group, an aralkylthio group, a N-nitrosoalkylamino group, an alkoxy group, a mercapto group and the like (when Y signifies a mercapto group, then the corresponding compound of formula VI is the iminothiol form of the corresponding thiolactam). The compounds of formula VI can be prepared from compounds of formula V according to methods known per se; see, for example, Belgian Patent Specifications Nos. 802 233, 833 249 and 865 653, U.S. Pat. No. 3,681,341 and J. Org. Chemistry 29, 231 (1964), which are incorporated herein for reference.

Various Examples hereinafter contain detailed information concerning the preparation of compounds of formula VI from compounds of formula V.

The reaction of a compound of formula VI with an isocyanoacetic acid alkyl ester of formula VII to give a compound of formula VIIIa is carried out in an inert solvent such as dimethylformamide, hexamethylphosphoric acid triamide, dimethyl sulphoxide, tetrahydrofuran or any other suitable organic solvent and in the presence of a base which is sufficiently strongly basic to form the anion of the isocyanoacetic acid alkyl ester of formula VII. Suitable bases are alkali metal alkoxides such as sodium methoxide or potassium t-butoxide, alkali metal hydrides such as sodium hydride, alkali metal amides such as lithium amide or lithium diisopropylamide, tertiary amines such as triethylamine, and the like. The reaction is conveniently carried out at a temperature between about −40° C. and about room temperature.

The compounds of formula VIIIb can be prepared from compounds of formula VIIIa in analogy to process variant (g) described above.

The hydrolysis of carboxylic acid esters of formulae VIIIa and VIIIb to give the carboxylic acids of formula II (i.e. formula IIa or IIb) is carried out according to methods which are known per se and familiar to any person skilled in the art. Conveniently, the hydrolysis is carried out under basic conditions, for example using aqueous basic solutions (e.g. aqueous sodium hydroxide, aqueous potassium carbonate solution or the like), optionally in the presence of a solubilizer (e.g. methanol, ethanol, tetrahydrofuran, dioxan or the like). If the compound of formula Ib is a t-alkyl ester (e.g. a t-butyl ester), then the hydrolysis is advantageously carried out under acidic conditions, for example using trifluoroacetic acid, aqueous mineral acids or the like.

The compounds of formula V used as starting materials belong to a class of substance known per se; specific members of this class of substance which have not previously been described can be prepared in analogy to the known members. Moreover, various Examples hereinafter contain detailed information concerning the preparation of compounds of formula V.

The compounds of formula III can be readily prepared from carboxylic acid azides of the formula

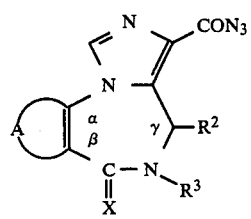

wherein A, X, $R^2$ and $R^3$ are as above.

For example, a carboxylic acid azide of formula IX can be reacted at an elevated temperature with an alcohol (e.g. methanol, ethanol, benzyl alcohol or the like) and the urethane obtained can be hydrolyzed. In a preferred embodiment, benzyl alcohol is used and the benzylurethane obtained is cleaved hydrogenolytically according to methods which are known per se and familiar to any person skilled in the art.

The carboxylic acid acides of formula IX can be prepared, for example, by treating a carboxylic acid ester of formula VIIIa or VIIIb with hydrazine and reacting the hydrazide obtained with sodium nitrate in the presence of an acid such as acetic acid.

The compounds of formulae IV and X used as starting materials can be prepared starting from compounds of formula VIII (i.e. formulae VIIIa and VIIIb) in accordance with Formula Scheme 2 hereinafter in which A, X, Z, $R^2$, $R^3$ and $R^7$ are as above and $R^{61}$ is lower alkyl:

Formula Scheme 2

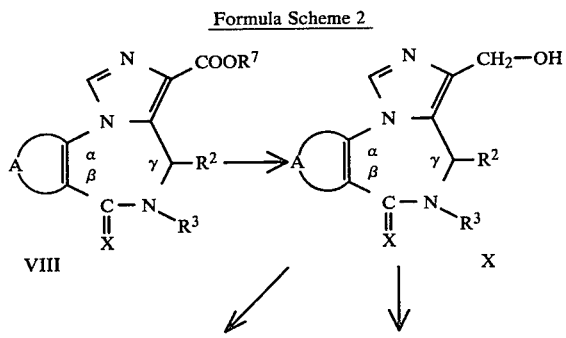

-continued
Formula Scheme 2

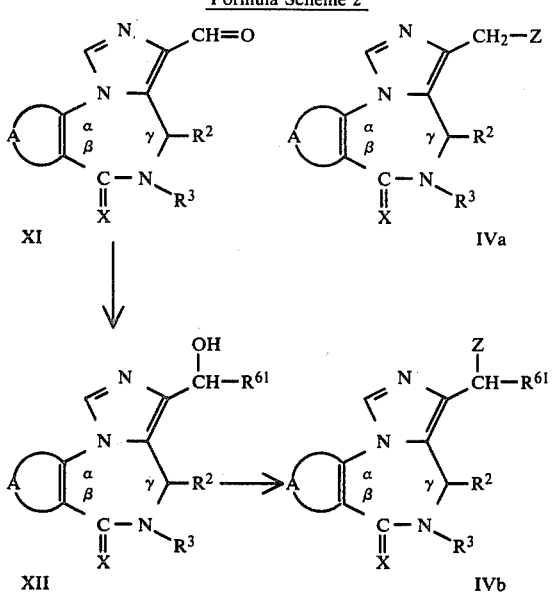

The reduction of a carboxylic acid ester of formula VIII to give an alcohol of formula X can be carried out using a reducing agent such as lithium borohydride in an inert organic solvent such as diethyl ether, tetrahydrofuran, dimethoxyethane or the like.

The oxidation of a compound of formula X to give an aldehyde or formula XI is conveniently carried out using a mild oxidizing agent such a manganese dioxide or the like in an inert organic solvent such as methylene chloride, chloroform or the like.

An aldehyde of formula XI can be reacted with a metal-organic compound yielding the group $R^{61}$ according to methods which are generally known and familiar to any person skilled in the art and there is thus obtained a compound of formula XII. Preferred metal-organic compounds are Grignard compounds such as methyl-magnesium iodide, ethyl-magnesium iodide, isopropyl-magnesium iodide, n-propyl-magnesium bromide, n-butyl-magnesium chloride and the like. Suitable solvents are ethers such as diethyl ether, tetrahydrofuran, t-butyl methyl ether, mixtures thereof and the like. Conveniently, the reaction is carried out at the boiling point of the reaction mixture, although it can, however, also be carried out at a lower temperature (e.g. at room temperature).

The preparation of compounds of formula IV (i.e. formulae IVa and IVb) from compounds of formula X or XII is carried out according to methods known per se. Corresponding halides can be prepared, for example, by treating compounds of formula X or XII with halogenating agents such as thionyl chloride, phosphorus oxychloride, phosphorus pentachloride, carbon tetrabromide/triphenylphosphine or the like.

The compounds of formulae III and IV used as starting materials are novel and are likewise objects of the present invention.

As mentioned earlier, the compounds of formula I are novel and have extremely valuable pharmacodynamic properties. They exhibit only a low toxicity and it has been known that they have a pronounced affinity to the central benzodiazepine receptors and are capable of antagonizing the central-depressant, muscle relaxant, ataxic, blood pressure-lowering and respiratory-depressant properties of 1,4-benzodiazepines which have tranquillizing activity.

The affinity of compounds of formula I to the central benzodiazepine receptors was determined according to the method described in Life Science 20, 2101–2110 (1977) and Science 198, 849–851 (1977). According to this method, the inhibition of the binding of tritiated diazepam at the specific benzodiazepine receptors in the cerebral cortex by the respective test substances is ascertained. The $IC_{50}$ ("50% inhibiting concentration") is that concentration of the respective test substance which brings about a 50 percent inhibition of the specific binding of the tritiated diazepam at the specific benzodiazepine receptors in the cerebral cortex.

One of the typical properties of 1,4-benzodiazepines, which have tranquillizing activity, in experimental animals is their pronounced anticonvulsant activity which can be demonstrated, for example, in the known and generally recognized pentetrazole test. This property was used to evaluate the test described hereinafter which permits the determination of compounds which are capable of antagonizing the central properties of 1,4-benzodiazepines which have tranquillizing activity.

In this test, 5 mg/kg (i.p.) of diazepam (i.e. a supramaximal dosage which in the pentetrazole test on more than 900 mice protects all experimental animals from convulsive attacks) were administered to mice 1 hour before the pentetrazole (120 mg/kg i.p.) and the compound to be tested was administered p.o. 15 minutes before the pentetrazole. The antagonistic activity of the compounds investigated, i.e. their ability to counteract the activity of the diazepam in the pentetrazole test, is determined by counting the mice which suffer convulsive attacks in this test.

In the following Table there are presented the results which have been obtained with representative members of the class of compound defined by formula I in the test previously described. The $ED_{50}$ value is given for each of the compounds listed in the Table. The $ED_{50}$ is the amount of test compound in mg/kg (p.o.) which in 50% of the animals counteracts the diazepam effect in the above test. Moreover, the Table contains the $IC_{50}$ value (defined above) for all test compounds listed therein.

TABLE

| Compound of formula I | | | | | | | | $IC_{50}$ in nM/l | $ED_{50}$ in mg/kg p.o. |
|---|---|---|---|---|---|---|---|---|---|
| A | $R^4$ | $R^5$ | $R^1$ | $R^2$ | $R^3$ | X | Configuration | | |
| (a) | H | Cl | Cl | H | —CH$_3$ | O | — | 3.6 | 0.9 |
| (a) | H | Cl | Cl | —CH=CH—CH$_2$— | | O | (R/S) | 3.9 | 1.0 |
| (a) | H | H | Cl | H | —CH$_3$ | O | — | 100 | 1.7 |
| (b) | — | — | Cl | —(CH$_2$)$_3$— | | O | (S) | 17 | 0.83 |
| (a) | F | H | Cl | H | —CH$_3$ | O | — | 28 | 2.3 |
| (a) | H | H | J | H | —CH$_3$ | O | — | 23 | 2.5 |
| (a) | H | H | —NO$_2$ | H | —CH$_3$ | O | — | 72 | 4.0 |
| (a) | H | H | Br | H | —CH$_3$ | O | — | 34 | 4.5 |
| (a) | H | Cl | H | H | —CH$_3$ | O | — | 110 | 6.2 |
| (a) | F | H | Br | H | —CH$_3$ | O | — | 51 | 7.1 |

TABLE-continued

| | | | Compound of formula I | | | | | IC$_{50}$ in | ED$_{50}$ in |
|---|---|---|---|---|---|---|---|---|---|
| A | R$^4$ | R$^5$ | R$^1$ | R$^2$ | R$^3$ | X | Configuration | nM/l | mg/kg p.o. |
| (a) | H | H | Cl | H | —CH$_3$ | S | — | 250 | 10.5 |
| (a) | H | H | Cl | —(CH$_2$)$_3$— | | O | (S) | 120 | 8.0 |
| (a) | H | H | Br | —(CH$_2$)$_3$— | | O | (S) | 48 | 9.9 |
| (a) | H | Cl | H | —CH=CH—CH$_2$— | | O | (R/S) | 240 | 10.9 |
| (a) | H | Cl | —CH$_2$OCH$_3$ | H | —CH$_3$ | O | — | 30 | 1.4 |
| (a) | H | H | —CH$_2$OCH$_3$ | H | —CH$_3$ | O | — | 380 | 8.9 |

As mentioned earlier, the compounds of formula I antagonize the central-depressant, muscle relaxant, ataxic, blood pressure-lowering and respiratory-depressant properties of 1,4-benzodiazepines which have tranquillizing activity. The latter are in widespread use in therapy and are often administered in high dosages, so that the above-mentioned activities can also appear strongly as side-effects. The compounds of formula I can be used as antidotes in the case of intoxications in which excessive intake of 1,4-benzodiazepines which have tranquillizing activity is concerned. They are also suitable for shortening anaesthesia in surgery and in obstetrics induced by 1,4-benzodiazepines which have tranquillizing activity. In the case of neonatals, a possible respiratory depression, which deteriorates upon the administration of 1,4-benzodiazepines which have tranquillizing activity to the mother, can be counteracted. The compounds of formula I can also be used to suppress, in the case of 1,4-benzodiazepines which are used in other fields of indication, the activities on the central nervous system which are undesirable in such a case. Examples of such 1,4-benzodiazepines which can be used in other fields of indication are the schistosomicidally-active 1,4-benzodiazepines described in British Patent Specifications Nos. 1 444 529 and 1 474 305 (incorporated by reference) such as (+)-5-(o-chlorophenyl)-1,3-dihydro-3-methyl-7-nitro-2H-1,4-benzodiazepin-2-one.

The compounds of formula I and their pharmaceutically acceptable acid addition salts can be used as medicaments, for example, in the form of pharmaceutical preparations. The pharmaceutical preparations can be administered orally (e.g. in the form of tablets, coated tablets, dragées, hard and soft gelatine capsules, solutions, emulsions or suspensions). The administration can, however, also be carried out rectally (e.g. in the form of suppositories) or parenterally (e.g. in the form of injection solutions).

For the manufacture of tablets, coated tablets, dragées and hard gelatine capsules, the compounds of formula I and their pharmaceutically acceptable acid addition salts can be processed with pharmaceutically inert, inorganic or organic carriers. Examples of such carriers which can be used for tablets, dragées and hard gelatine capsules are lactose, maize starch or derivatives thereof, talc, stearic acid or its salts etc. Suitable carriers for soft gelatine capsules are, for example, vegetable oils, waxes, fats, semi-solid and liquid polyols etc. Suitable carriers for the manufacture of solutions and syrups are, for example, water, polyols, saccharose, invert sugar, glucose and the like. Suitable carriers for injection solutions are, for example, water, alcohols, polyols, glycerine, vegetable oils etc. Suitable carriers for suppositories are, for example, natural or hardened oils, waxes, fats, semi-liquid or liquid polyols and the like.

The pharmaceutical preparations can also contain preserving agents, solubilizing agents, stabilizing agents, wetting agents, emulsifying agents, sweetening agents, colouring agents, flavouring agents, salts for the variation of the osmotic pressure, buffers, coating agents or antioxidants. They can also contain still other therapeutically valuable substances.

As mentioned earlier, compounds of general formula I and pharmaceutically acceptable acid addition salts thereof can be used in the control or prevention of illnesses, especially in the antagonization of the central-depressant, muscle relaxant, ataxic, blood pressure-lowering and respiratory-depressant properties of 1,4-benzodiazepines which have tranqualizing activity. In particular, compounds of formula I can be used in combination with the schistosomicidally-active compounds mentioned above, for example, in combination with (+)-5-(o-chlorophenyl)-1,3-dihydro-3-methyl-7-nitro-2H-1,4-benzodiazepin-2-one, in the control of schistosomiasis. In this case, the compounds of formula I or their pharmaceutically acceptable acid addition salts can be administered before, simultaneously with or after the administration or intake of 1,4-benzodiazepines which have tranquillizing activity. If the compound of formula I or a pharmaceutically acceptable acid addition salt thereof is administered simultaneously with the 1,4-benzodiazepine which has tranquillizing activity, then the administration can be as an ad-hoc combination or in the form of a pharmaceutical combination which contains a compound of general formula I or a pharmaceutically acceptable acid addition salt thereof and a 1,4-benzodiazepine derivative which has tranquillizing activity; such pharmaceutical combinations are likewise an object of the present invention. The dosage of the compounds of formula I and their pharmaceutically acceptable acid addition salts can vary within wide limits and is, of course, fitted to the individual requirements in each particular case. In general, a daily dosage of about 0.2 mg to about 500 mg should be appropriate.

As mentioned earlier, medicaments containing a compound of formula I or a pharmaceutically acceptable acid addition salt thereof are likewise an object of the present invention as is also a process for the manufacture of such medicaments which comprises bringing one or more compounds of formula I or pharmaceutically acceptable acid addition salts thereof and, if desired, one or more other therapeutically valuable substances into a galenical administration form; in this connection reference is again made to the pharmaceutical combinations mentioned above which are likewise an object of the present invention. In particular, pharmaceutical combinations containing a compound of formula I and one of the schistosomicidally-active compounds mentioned above, especially (+)-5-(o-chlorophenyl)-1,3-dihydro-3-methyl-7-nitro-2H-1,4-benzodiazepin-2-one, are an object of the present invention. Such combinations are suitable for the control of schistosomiasis.

In the following Examples, which illustrate the present invention in more detail but in no way are intended to limit its extent, all temperatures are given in degrees Centigrade.

EXAMPLE 1

(a) 29.1 g (0.14 mol) of 6-chloroisatoic acid anhydride are stirred at 110° for 1 hour with 13.12 g (0.14 mol) of sarcosine in 150 ml of dimethyl sulphoxide. The solution obtained is concentrated and the residue is recrystallized from ethanol. There is obtained 6-chloro-3,4-dihydro-4-methyl-2H-1,4-benzodiazepine-2,5(1H)-dione of melting point 237°–238°.

(b) A solution of 10 g (44.5 mmol) of 6-chloro-3,4-dihydro-4-methyl-2H-1,4-benzodiazepine-2,5(1H)-dione in 100 ml of dimethylformamide is treated under an argon atmosphere with 5.50 g (49 mmol) of potassium t-butylate and the mixture is stirred for 20 minutes. The solution obtained is cooled to −30° and at this temperature there are added dropwise thereto 3.45 g (49 mmol) of diethylchlorophosphate. The mixture is subsequently stirred at −20° for 10 minutes.

In the meanwhile, a solution of 5.50 g (40 mmol) of potassium t-butylate in 10 ml of dimethylformamide is cooled in an acetone/dry-ice bath and treated with 5.54 g (49 mmol) of ethyl isocyanoacetate. The dark red solution is added at −10° to −20° to the mixture obtained according to the preceding paragraph and the resulting mixture is stirred for 0.5 hour without cooling before it is neutralized with 5 ml of glacial acetic acid and poured into about 300 ml of water. The orange solution is extracted three times with chloroform. The organic phase is washed five times with water, dried over magnesium sulphate and evaporated. By chromatography on silica gel and recrystallization from ethyl acetate there is obtained ethyl 7-chloro-5,6-dihydro-5-methyl-6-oxo-4H-imidazo-[1,5-a][1,4]benzodiazepine-3-carboxylate of melting point 229°–230°.

(c) A mixture of 3.11 g (9.72 mmol) of ethyl 7-chloro-5,6-dihydro-5-methyl-6-oxo-4H-imidazo[1,5-a][1,4]benzodiazepine-3-carboxylate, 10 ml of ethanol, 2 ml of water and 400 mg of sodium hydroxide is heated to boiling under reflux for 1 hour. After evaporation of the ethanol, the residue is treated with 10 ml of 1 N hydrochloric acid. The colourless material obtained is filtered off under suction, washed with water and dried. There is obtained 7-chloro-5,6-dihydro-5-methyl-6-oxo-4H-imidazo[1,5-a][1,4]benzodiazepine-3-carboxylic acid with a decomposition point of 283°–284°.

(d) 2.69 g of 7-chloro-5,6-dihydro-5-methyl-6-oxo-4H-imidazo[1,5-a][1,4]benzodiazepine-3-carboxylic acid are heated to 290°. After completion of the carbon dioxide evolution, the brown melt is cooled and taken up in chloroform. This solution is filtered over a silica gel column and evaporated. There is obtained 7-chloro-4,5-dihydro-5-methyl-6H-imidazo[1,5-a][1,4]benzodiazepin-6-one of melting point 200°–201°.

EXAMPLE 2

1.30 g (5.25 mmol) of 7-chloro-4,5-dihydro-5-methyl-6H-imidazo[1,5-a][1,4]benzodiazepin-6-one are stirred at 90° for 30 minutes in 10 ml of dimethylformamide with 800 mg (6 mmol) of N-chlorosuccinimide. Subsequently, the mixture is poured into water and extracted with chloroform. The combined chloroform extracts are washed with water, dried over magnesium sulphate and evaporated. By column chromatography on silica gel there is obtained 3,7-dichloro-4,5-dihydro-5-methyl-6H-imidazo[1,5-a][1,4]benzodiazepin-6-one of melting point 211°–212°.

EXAMPLE 3

(a) A mixture of 175 g (0.93 mol) of methyl 3-amino-2-thiophenecarboxylate hydrochloride, 1.8 l of n-butanol and 77 g of sodium hydroxide is heated to boiling under reflux for 30 minutes. After concentration of the suspension obtained, the resulting mixture of sodium salt of 3-amino-2-thiophenecarboxylic acid and sodium chloride is used directly for the next step. For this purpose, the mixture is treated with 800 ml of water, 280 ml of concentrated hydrochloric acid and 230 ml of tetrahydrofuran. At 15° to 25° phosgene is conducted through this mixture and subsequently air is conducted through the mixture for 15 minutes. The precipitated solid material is filtered off under suction, washed with water and dried. There is obtained 2H-thieno[3,2-d][1,3]oxazine-2,4(1H)-dione of melting point 220°–221°.

(b) A solution of 34.3 g (202 mmol) of 2H-thieno[3,2-d][1,3]oxazine-2,4(1H)-dione and 23.3 g (202 mmol) of L-proline in 200 ml of dimethyl sulphoxide is stirred at 110° for 1 hour. The brown solution obtained is poured into 2 l of water and stirred at room temperature overnight. The precipitated product is filtered off under suction, dried in vacuo and washed with about 200 ml of boiling ethyl acetate. There is thus obtained (S)-5a,6,7,8-tetrahydro-5H-pyrrolo[1,2-a]thieno[3,2-e][1,4]diazepine-5,10(4)-dione of melting point 244°–247°.

(c) 7 g (31.5 mmol) of (S)-5a,6,7,8-tetrahydro-5H-pyrrolo[1,2-a]thieno[3,2-e][1,4]diazepine-5,10(4)-dione are suspended in 30 ml of dimethylformamide under an argon atmosphere and treated at −50° with 3.92 g (35 mmol) of potassium t-butylate. The solution is stirred for 10 minutes at −50°, at this temperature there are added dropwise thereto 6.0 g (35 mmol) of diethylchlorophosphate and the mixture is stirred for 0.5 hour.

Separately, 3.92 g (35 mmol) of potassium t-butylate are dissolved in 7 ml of dimethylformamide, the solution is cooled in an acetone/dry-ice bath and treated with 3.95 g (35 mmol) of ethyl isocyanoacetate. The orange coloured solution obtained is added dropwise at −50° to the mixture obtained according to the preceding paragraph. Subsequently, the mixture is stirred at −50° to −60° for a further 10 minutes, neutralized with 3.2 ml of acetic acid and poured into about 250 ml of water. The mixture is extracted twice with 200 ml of chloroform each time, the combined chloroform phases are washed five times with 300 ml of water each time, dried over magnesium sulphate and evaporated. By column chromatography on silica gel and subsequent recrystallization from ethyl acetate there is obtained ethyl (S)-10,11,12,12a-tetrahydro-8-oxo-8H-imidazo[5,1-c]pyrrolo(1,2-a]thieno[3,2-e]-[1,4]diazepine-1-carboxylate of melting point 212.5°–213°.

(d) A mixture of 6.34 g (20 mmol) of ethyl (S)-10,11,12,12a-tetrahydro-8-oxo-8H-imidazo[5,1-c]pyrrolo[1,2-a] thieno[3,2-e][1,4]diazepine-1-carboxylate, 956 mg (23.9 mmol) of sodium hydroxide, 20 ml of ethanol and 4 ml of water is heated to boiling under reflux for 30 minutes. After evaporation of the ethanol, the residue is treated with 23.9 ml of 1 N hydrochloric acid. The white material obtained is filtered off under suction, washed with water and dried. There is obtained (S)-10,11,12,12a-tetrahydro-8-oxo-8H-imidazo[5,1-c]pyrrolo[1,2-a]thieno[3,2-e]diazepine-1-carboxylic acid of melting point 259°.

(e) 5.38 g (18.6 mmol) of (S)-10,11,12,12a-tetrahydro-8-oxo-8H-imidazo[5,1-c]pyrrolo[1,2-a]thieno[3,2-e]diazepine-1-carboxylic acid are heated to 270°. After completion of the carbon dioxide evolution, the melt is taken up in ethyl acetate and stirred for 10 minutes. The solid material is filtered off under suction and dried. There is obtained (S)-10,11,12,12a-tetrahydro-8H-imidazo[5,1-c]pyrrolo[1,2-a]thieno[3,2-e][1,4]diazepin-8-one of melting point 228°–230°.

EXAMPLE 4

3.0 (12.2 mmol) of (S)-10,11,12,12a-tetrahydro-8H-imidazo[5,1-c]pyrrolo[1,2-a]thieno[3,2-e][1,4]diazepin-8-one in 20 ml of dimethylformamide are stirred at 65° for 40 minutes with 1.63 g (12.2 mmol) of N-chlorosuccinimide. The solution is poured into water and extracted with chloroform. The organic phase is washed several times with water, dried over magnesium sulphate and evaporated. By column chromatography on silica gel there is obtained (S)-1-chloro-10,11,12,12a-tetrahydro-8H-imidazo[5,1-c]pyrrolo[1,2-a]thieno[3,2-e][1,4]diazepin-8 one of melting point 180°–183°.

EXAMPLE 5

(a) A mixture of 4.8 g (24.3 mmol) of 6-chloroisatoic acid anhydride, 2.83 g (25 mmol) of (S)-3,4-dehydroproline and 20 ml of dimethyl sulphoxide is stirred at 100° for 1.25 hours. Subsequently, the mixture is poured into 200 ml of water and extracted three times with ethyl acetate. The organic phase is washed once with water, dried over magnesium sulphate and evaporated. The residue is chromatographed on silica gel and the material obtained is crystallized from ethyl acetate. There is obtained (S)-6-chloro-3,11a-dihydro-5H-pyrrolo[2,1-c][1,4]benzodiazepine-5,11(10H)-dione of melting point 250°.

(b) A suspension of 0.67 g (15.4 mmol) of sodium hydride (55 percent oil dispersion) in 25 ml of dry dimethylformamide is treated with 3.22 g (12.9 mmol) of (S)-6-chloro-3,11a-dihydro-5H-pyrrolo[2,1-c][1,4]benzodiazepine-5,11(10H)-dione and the mixture is stirred for 30 minutes. Subsequently, the mixture is cooled to −35°, 2.1 ml (13.4 mmol) of diethylchlorophosphate are added dropwise thereto and the mixture obtained is stirred for about a further 15 minutes.

A solution of 1.55 g (14.2 mmol) of potassium t-butylate in 5.5 ml of dry dimethylformamide is cooled in an acetone/dry-ice bath, treated with 1.8 ml (14.2 mmol) of ethyl isocyanoacetate and added dropwise at −10° to the mixture obtained according to the preceding paragraph. The cooling bath is removed, the mixture is neutralized at room temperature with glacial acetic acid, poured into 150 ml of water and extracted three times with chloroform. The chloroform extracts are washed once with water, dried over magnesium sulphate and evaporated. The residue is chromatographed on silica gel and the material obtained is recrystallized from ethyl acetate. There is obtained ethyl (R,S)-8-chloro-11,13a-dihydro-9-oxo-9H-imidazo[1,5-a]pyrrolo[2,1-c][1,4]benzodiazepine-1-carboxylate of melting point 204°–206°.

(c) A mixture of 1.1 g (3.2 mmol) of ethyl (R,S)-8-chloro-11,13a-dihydro-9-oxo-9H-imidazo[1,5-a]pyrrolo[2,1-c][1,4]benzodiazepine-1-carboxylate and 0.187 g (4.7 mmol) of sodium hydroxide is treated with 5 ml of water and 15 ml of ethanol and heated to boiling under reflux for 0.5 hours. The mixture is treated with 4.7 ml of 1 N hydrochloric acid, evaporated until crystallization begins, diluted with about 50 ml of water and left to stand in an ice-bath for 1 hour. The precipitated material is filtered off under suction, washed with water and dried. There is obtained (R,S)-8-chloro-11,13a-dihydro-9-oxo-9H-imidazo[1,5-a]pyrrolo[2,1-c][1,4]benzodiazepine-1-carboxylic acid of melting point 249°.

(d) 0.8 g (2.5 mmol) of (R,S)-8-chloro-11,13a-dihydro-9-oxo-9H-imidazo[1,5-a]pyrrolo[2,1-c][1,4]benzodiazepine-1-carboxylic acid are heated with a Bunsen burner until the evolution of carbon dioxide has ceased. Subsequently, the material is boiled with ethyl acetate, left to stand for a short time and the solid material is filtered off under suction. There is obtained (R,S)-8-chloro-11,13a-dihydro-9H-imidazo[1,5-a]pyrrolo[2,1-c][1,4]benzodiazepin-9-one of melting point 271°–273°.

EXAMPLE 6

1.3 g (4.8 mmol) of (R,S)-8-chloro-11,13a-dihydro-9H-imidazo[1,5-a]pyrrolo[2,1-c][1,4]benzodiazepin-9-one and 0.64 g (4.8 mmol) of N-chlorosuccinimide are treated with 20 ml of dimethylformamide and stirred at 100° for 40 minutes. Subsequently, the mixture is poured into 80 ml of water and extracted four times with chloroform. The chloroform extracts are washed three times with water, dried over magnesium sulphate and evaporated. The residue is chromatographed on silica gel using ethyl acetate/chloroform (1:3) for the elution. After recrystallization from ethyl acetate/hexane, there is obtained (R,S)-1,8-dichloro-11,13a-dihydro-9H-imidazo[1,5-a]pyrrolo[2,1-c]-[1,4]benzodiazepin-9-one of melting point 235°–237°.

EXAMPLE 7

(a) 24 g (132.5 mmol) of 5-fluoroisatoic acid anhydride are dissolved in 140 ml of dimethyl sulphoxide and treated with 11.8 g (132.5 mmol) of sarcosine. The solution is stirred at 100° until the gas evolution ceases (duration: about 1.5 hours) and subsequently poured into about 1.2 l of water. After stirring for 10 minutes, a solid material crystallizes out. The crystals are filtered off under suction, washed with 1 l of water and dried. There is obtained 7-fluoro-3,4-dihydro-4-methyl-2H-1,4-benzodiazepine-2,5(1H)-dione of melting point 262°–263°.

(b) A solution of 6.5 g (32 mmol) of 7-fluoro-3,4-dihydro-4-methyl-2H-1,4-benzodiazepine-2,5(1H)-dione in 30 ml of dry dimethylformamide is treated with 4.3 g (38 mmol) of potassium t-butylate under an argon atmosphere. The temperature thereby rises to 35°. After 10 minutes, the mixture is cooled to −30° and 5.8 g (34 mmol) of diethylchlorophosphate are added dropwise thereto at −30° to −20°. The resulting solution is subsequently stirred at −20° for 10 minutes.

Separately, 4 g (35 mmol) of potassium t-butylate are dissolved in 10 ml of dimethylformamide and treated at about −40° with 4 g (35 mmol) of ethyl isocyanoacetate. This solution is added dropwise at −10° to −20° to the above mixture obtained according to the preceding paragraph. The resulting mixture is then stirred without cooling for 1 hour, 3.2 ml of glacial acetic acid are added thereto, the mixture is poured into about 400 ml of water and extracted three times with 150 ml of ethyl acetate each time. The combined organic extracts are washed five times with 200 ml of water each time, dried over magnesium sulphate and evaporated. From the oily residue there is obtained by column chromatography on silica gel and subsequent recrystallization from ethyl acetate/ether ethyl 8-fluoro-5,6-dihydro-5- methyl-6-oxo-4H-imidazo[1,5-a][1,4]benzodiazepine-3-carboxylate of melting point 199°–200°.

(c) A solution of 3.03 g (10 mmol) of ethyl 8-fluoro-5,6-dihydro-5-methyl-6-oxo-4H-imidazo[1,5-a][1,4]-benzodiazepine-3-carboxylate and 0.44 g (11 mmol) of sodium hydroxide in 20 ml of ethanol and 10 ml of water is heated to boiling under reflux for 30 minutes. Subsequently, the mixture is treated with 11 ml of 1 N hydrochloric acid and concentrated to half of the volume. The precipitated crystals are filtered off under suction and dried. There is obtained 8-fluoro-5,6-dihydro-5-methyl-6-oxo-4H-imidazo[1,5-a][1,4]benzodiazepine-3-carboxylic acid of decomposition point 279°.

(d) 9.2 g of 8-fluoro-5,6-dihydro-5-methyl-6-oxo-4H-imidazo[1,5-a][1,4]benzodiazepine-3-carboxylic acid are heated to 290°. After completion of the carbon dioxide evolution, the product is dissolved in chloroform and treated with hexane. The precipitated crystals are filtered off under suction and dried. There is obtained 8-fluoro-4,5-dihydro-5-methyl-6H-imidazo[1,5-a][1,4]-benzodiazepin-6-one of melting point 236°.

EXAMPLE 8

2.31 g (10 mmol) of 8-fluoro-4,5-dihydro-5-methyl-6H-imidazo[1,5-a][1,4]benzodiazepin-6-one and 1.47 g (11 mmol) of N-chlorosuccinimide are heated to 100° for 30 minutes in dimethylformamide. Subsequently, the mixture is poured into water and extracted several times with chloroform. The combined chloroform extracts are washed with water, dried over magnesium sulphate and evaporated. The residue is recrystallized from ethyl acetate and yields 3-chloro-8-fluoro-4,5-dihydro-5-methyl-6H-imidazo[1,5-a][1,4]benzodiazepin-6-one of melting point 217°–218°.

EXAMPLE 9

3.58 g of N-bromosuccinimide are added to 4.62 g (20 mmol) of 8-fluoro-4,5-dihydro-5-methyl-6H-imidazo[1,5-a][1,4]benzodiazepin-6-one in 100 ml of dimethylformamide and the mixture is stirred at room temperature for 2 hours. Subsequently, the mixture is poured into 500 ml of water and extracted several times with chloroform. The combined chloroform extracts are washed with water, dried over magnesium sulphate and evaporated. After recrystallization of the residue from ethyl acetate, there is obtained 3-bromo-8-fluoro-4,5-dihydro-5-methyl-6H-imidazo[1,5-a][1,4]benzodiazepin-6-one of melting point 200°.

EXAMPLE 10

(a) 19.0 g (0.10 mol) of 3,4-dihydro-4-methyl-2H-1,4-benzodiazepine-2,5(1H)-dione are placed in 100 ml of dry dimethylformamide under an argon atmosphere. 15.5 g (0.12 mol) of potassium t-butylate are added thereto, the temperature rising from 25° to 39°. The mixture is cooled to room temperature and 18.2 g (0.105 mol) of diethylchlorophosphate are added dropwise thereto at a temperature between 18° and 22°.

Separately, 11.2 g (0.10 mol) of potassium t-butylate are dissolved in 30 ml of dimethylformamide. This solution is cooled to about −50° and treated under argon with 11.3 g (0.10 mol) of ethyl isocyanoacetate. Subsequently, this solution is added dropwise at 18° to 23° while cooling to the mixture obtained according to the preceding paragraph. The resulting mixture is stirred at room temperature for 1 hour, 5 ml of acetic acid are added thereto, then the mixture is poured into 500 ml of water and extracted twice with 200 ml of chloroform each time. The combined chloroform extracts are washed three times with 300 ml of water each time, dried over magnesium sulphate and evaporated. 150 ml of ethyl acetate are added to the oily residue and it is left to crystallize at 0°. The separated crystals are filtered off under suction and washed with cold ethyl acetate to give ethyl 5,6-dihydro-5-methyl-6-oxo-4H-imidazo[1,5-a][1,4]benzodiazepine-3-carboxylate of melting point 163°–165°. After recrystallization from ethyl acetate, the product has a melting point of 164°–165°.

(b) 50 g (187.3 mmol) of ethyl 5,6-dihydro-5-methyl-6-oxo-4H-imidazo[1,5-a][1,4]benzodiazepine-3-carboxylate in 400 ml of ethanol are heated to boiling under reflux for 2 hours together with 150 ml of hydrazine hydrate. The precipitated material is filtered off under suction and dried. There is obtained 5,6-dihydro-5-methyl-6-oxo-4H-imidazo[1,5-a][1,4]benzodiazepine-3-carboxylic acid hydrazide of melting point 312°–313°.

(c) A solution of 19 g (70 mmol) of 5,6-dihydro-5-methyl-6-oxo-4H-imidazo[1,5-a][1,4]benzodiazepine-3-carboxylic acid hydrazide in 60 ml of water and 150 ml of glacial acetic acid is treated dropwise at 0° to 5° with a solution of 16.5 g of sodium nitrite in 30 ml of water. The white suspension is subsequently stirred in an ice-bath for 1 hour and cautiously poured into 150 g of sodium carbonate in 400 ml of water. The precipitated material is filtered off under suction, washed with water and dried. There is obtained 5,6-dihydro-5-methyl-6-oxo-4H-imidazo[1,5-a][1,4]benzodiazepine-3-carboxylic acid azide which decomposes at 160°.

(d) 17 g of 5,6-dihydro-5-methyl-6-oxo-4H-imidazo[1,5-a][1,4]benzodiazepine-3-carboxylic acid azide are stirred at 110° for 7 hours with 150 ml of benzyl alcohol. The solution is concentrated to half of the volume and diluted with ethanol. The precipitated material is filtered off under suction, washed with ethanol and dried. There is obtained benzyl 5,6-dihydro-5-methyl-6-oxo-4H-imidazo[1,5-a][1,4]benzodiazepine-3-carbamate of melting point 246°–247°.

(e) 34 g (93.8 mmol) of benzyl 5,6-dihydro-5-methyl-6-oxo-4H-imidazo[1,5-a][1,4]benzodiazepine-3-carbamate are hydrogenated at room temperature and normal pressure in 300 ml of methanol in the presence of 4 g of 10 percent palladium/carbon. After removal of the catalyst and evaporation, the residue is recrystallized from ethyl acetate and hexane. There is obtained 3-amino-4,5-dihydro-5-methyl-6H-imidazo[1,5-a][1,4]benzodiazepin-6-one of melting point 202°–204°.

(f) A solution of 5 g (22 mmol) of 3-amino-4,5-dihydro-5-methyl-6H-imidazo[1,5-a][1,4]benzodiazepin-6-one in 100 ml of hydrofluoboric acid (50 percent in water) is diazotized at 0° to 5° with a solution of 1.95 g (28 mmol) of sodium nitrite in 4 ml of water. The yellow solution is stirred in an ice-bath for 20 minutes, diluted with 85 ml of hydrofluoboric acid, poured into a quartz vessel and irradiated overnight with a UV-lamp. Subsequently, the mixture is extracted with chloroform. The chloroform extracts are washed with water, dried over magnesium sulphate and evaporated. By chromatography of the residue on a silica gel column there is obtained 3-fluoro-4,5-dihydro-5-methyl-6H-imidazo[1,5-a][1,4]benzodiazepin-6-one of melting point 171°–172°.

EXAMPLE 11

A solution of 1.08 ml (40 mmol) of 90 percent hydrogen peroxide in 20 ml of methylene chloride is treated dropwise at 5° to 10° with 6.80 ml (48 mmol) of trifluoroacetic acid anhydride and the mixture is stirred in an ice-bath for 10 minutes. The cooling bath is removed and there is added dropwise over a period of 15 minutes a suspension of 2.28 g (10 mmol) of 3-amino-4,5-dihydro-5-methyl-6H-imidazo[1,5-a][1,4]benzodiazepin-6-one in 20 ml of methylene chloride. The temperature rises to the boiling point. The mixture is subsequently stirred at the boiling point for a further 1 hour. The mixture is subsequently cooled and washed four times with water and twice with saturated sodium bicarbonate solution. The organic phase is dried over magnesium sulphate and evaporated. By recrystallization from ethyl acetate there is obtained 4,5-dihydro-5-methyl-3-nitro-6H-imidazo[1,5-a][1,4]benzodiazepin-6-one of melting point 227°–229°.

EXAMPLE 12

(a) A solution of 14.26 g (0.05 mol) of ethyl 5,6-dihydro-5-methyl-6-oxo-4H-imidazo[1,5-a][1,4]benzodiazepine-3-carboxylate and 2.2 g (0.055 mol) of sodium hydroxide in 100 ml of ethanol and 20 ml of water is heated to boiling under reflux for 45 minutes and subsequently treated with 55 ml of 1 N hydrochloric acid and 50 ml of water. After distilling off the ethanol, the resulting crystal slurry is filtered off under suction, washed with water and dried. There is obtained 5,6-dihydro-5-methyl-6-oxo-4H-imidazo[1,5-a][1,4]benzodiazepine-3-carboxylic acid of melting point 287°.

(b) 8.2 g of 5,6-dihydro-5-methyl-6-oxo-4H-imidazo[1,5-a][1,4]benzodiazepine-3-carboxylic acid are heated to 300°. After completion of the carbon dioxide evolution, the residue is left to cool and the material is recrystallized from chloroform/hexane. After drying, there is obtained 4,5-dihydro-5-methyl-6H-imidazo[1,5-a][1,4]benzodiazepin-6-one of melting point 212°–213°.

EXAMPLE 13

5 g (23.5 mmol) of 4,5-dihydro-5-methyl-6H-imidazo[1,5-a][1,4]benzodiazepin-6-one in 30 ml of dimethylformamide are treated with 3.20 g (23.5 mmol) of N-chlorosuccinimide and stirred at room temperature for 1.5 hours and at 60° for 10 minutes. The clear brown solution is poured into about 200 ml of water and extracted three times with chloroform. The combined chloroform extracts are washed with water, dried over magnesium sulphate and evaporated. By chromatography of the residue on a silica gel column and subsequent recrystallization from ethyl acetate there is obtained 3-chloro-4,5-dihydro-5-methyl-6H-imidazo[1,5-a][1,4]benzodiazepin-6-one of melting point 193°–194°.

EXAMPLE 14

20 g (93.8 mmol) of 4,5-dihydro-5-methyl-6H-imidazo[1,5-a][1,4]benzodiazepin-6 -one in 100 ml of dimethylformamide are treated with 17.5 g (98 mmol) of N-bromosuccinimide and stirred at room temperature for 35 minutes. The solution is poured into water and extracted twice with chloroform. The chloroform extracts are washed several times with water, dried over magnesium sulphate and evaporated. After recrystallization from ethyl acetate, the residue yields 3-bromo-4,5-dihydro-5-methyl-6H-imidazo[1,5-a][1,4]benzodiazepin-6-one of melting point 196°–198°.

EXAMPLE 15

1.06 g (5 mmol) of 4,5-dihydro-5-methyl-6H-imidazo[1,5-a][1,4]benzodiazepin-6-one are stirred at 90° for 40 hours together with 1.26 g of iodine in 20 ml of dimethylformamide. The mixture is poured into water and extracted three times with chloroform. The chloroform extracts are washed five times with water, dried over magnesium sulphate and evaporated. By chromatography of the residue on a silica gel column there is obtained 4,5-dihydro-3-iodo-5-methyl-6H-imidazo[1,5-a][1,4]benzodiazepin-6-one of melting point 174°–176°.

EXAMPLE 16

3.71 g (15 mmol) of 3-chloro-4,5-dihydro-5-methyl-6H-imidazo[1,5-a][1,4]benzodiazepin-6-one in 10 ml of toluene are heated to boiling under reflux for 4 hours together with 3.03 g (7.5 mmol) of 2,4-bis(p-methoxyphenyl)-1,3,2,4-dithiadiphosphetane-2,4-disulphide. The solution is washed with water and evaporated. By chromatography on a silica gel column and subsequent recrystallization from ethyl acetate there is obtained 3-chloro-4,5-dihydro-5-methyl-6H-imidazo[1,5-a][1,4]benzodiazepine-6-thione of melting point 197.5°–198.5°.

EXAMPLE 17

(a) 21.5 g (75.4 mmol) of ethyl 5,6-dihydro-5-methyl-6-oxo-4H-imidazo[1,5-a][1,4]benzodiazepine-3-carboxylate are dissolved in 250 ml of hot absolute tetrahydrofuran (filtered over Alox basic I) under an argon atmosphere while stirring, cooled to about 30° and treated dropwise with a solution of 1.66 g (75.4 mmol) of lithium borohydride. The mixture is heated to boiling under reflux for 6 hours, cooled to room temperature and treated with 50 ml of 3 N aqueous hydrochloric acid. The mixture is stirred at 60° for a further 2 hours and the tetrahydrofuran is removed in vacuo. The residue is made alkaline with concentrated ammonia and left to stand in an ice-bath for 2 hours. The crude product is filtered off under suction, washed with a large amount of water and recrystallized from ethanol. There is obtained 4,5-dihydro-3-(hydroxymethyl)-5-methyl-6H-imidazo[1,5-a][1,4]benzodiazepin-6-one of melting point 224°–226°.

(b) 6 g (24.6 mmol) of 4,5-dihydro-3-(hydroxymethyl)-5-methyl-6H-imidazo[1,5-a][1,4]benzodiazepin-6-one and 4.45 g of thionyl chloride are heated to boiling under reflux for 2 hours in 50 ml of benzene. The mixture is evaporated to dryness, the residue is taken up in chloroform and washed with 2 N sodium hydroxide. The organic phase is dried over magnesium sulphate and, after removal of the solvent, there is obtained 3-(chloromethyl)-4,5-dihydro-5-methyl-6H-imidazo[1,5-a][1,4]benzodiazepin-6-one of melting point 277°–280°.

(c) 1.30 g (5 mmol) of 3-(chloromethyl)-4,5-dihydro-5-methyl-6H-imidazo[1,5-a][1,4]benzodiazepin-6-one and 200 mg (5 mmol) of sodium hydroxide are hydrogenated at room temperature and normal pressure in 20 ml of alcohol and in the presence of 100 mg of 10 percent palladium/carbon. The catalyst is removed, the solvent is evaporated and the residue is taken up in chloroform. The solution is washed with water, dried over magnesium sulphate and evaporated. There is obtained 4,5-dihydro-3,5-dimethyl-6H-imidazo[1,5-a][1,4]benzodiazepin-6-one of melting point 184.5°–185.5°.

EXAMPLE 18

(a) A solution of 35 g (0.14 mmol) of (S)-(+)-7-chloro-1,2,3,11a-tetrahydro-5H-pyrrolo[2,1-c][1,4]benzodiazepine-5,11(10H)-dione in 170 ml of dry dimethylformamide is treated under an argon atmosphere with 17.3 g (0.15 mol) of potassium t-butylate, the temperature rising from 24° to 40°. The mixture is cooled to −30° and 25 g (0.15 mol) of diethylchlorophosphate are added dropwise thereto at a temperature between −30° and −20°.

Separately, 16.8 g of potassium t-butylate (0.15 mol) are dissolved in 50 ml of dimethylformamide. This solution is cooled to about −50° and treated under argon with 17.42 g (0.15 mol) of ethyl isocyanoacetate. Subsequently, this solution is added dropwise at −20° to −10° to the mixture obtained according to the preceding paragraph. The mixture is stirred without cooling for 1 hour, 14 ml of acetic acid are added thereto, the mixture is subsequently poured into about 1000 ml of water and extracted three times with 250 ml of chloroform each time. The combined chloroform phases are washed five times with 300 ml of water each time, dried over magnesium sulphate and evaporated. The residue is recrystallized from 500 ml of ethyl acetate. There is obtained (S)-(+)-ethyl-7-chloro-11,12,13,13a-tetrahydro-9-oxo-9H-imidazo[1,5-a]pyrrolo[2,1-c][1,4]benzodiazepine-1-carboxylate of melting point 242°–244°.

(b) 7 g (20.2 mmol) of (S)-(+)-ethyl-7-chloro-11,12,13,13a-tetrahydro-9-oxo-9H-imidazo[1,5-a]pyrrolo[2,1-c][1,4]benzodiazepine-1-carboxylate and 950 mg (23.8 mmol) of sodium hydroxide are heated to boiling under reflux for 30 minutes in 20 ml of alcohol and 4 ml of water. After evaporation of the ethanol, the residue is made acid with 23.7 ml of 1 N hydrochloric acid. The white material obtained is filtered off under suction, washed with a small amount of water and dried. There is obtained (S)-7-chloro-11,12,13,13a-tetrahydro-9-oxo-9H-imidazo[1,5-a]pyrrolo[2,1-c][1,4]benzodiazepine-1-carboxylic acid of melting point 227°.

(c) 5.8 g (18.2 mmol) of (S)-7-chloro-11,12,13,13a-tetrahydro-9-oxo-9H-imidazo[1,5-a]pyrrolo[2,1-c][1,4]benzodiazepine-1-carboxylic acid are heated to 230°. After completion of the carbon dioxide evolution, the melt is treated with ethyl acetate. The solid material is filtered off under suction and dried. There is obtained (S)-7-chloro-11,12,13,13a-tetrahydro-9H-imidazo[1,5-a]pyrrolo[2,1-c][1,4]benzodiazepin-9-one of melting point 216°–217°.

EXAMPLE 19

3 g (11 mmol) of (S)-7-chloro-11,12,13,13a-tetrahydro-9H-imidazo[1,5-a]pyrrolo[2,1-c][1,4]benzodiazepin-9-one in 30 ml of dimethylformamide are stirred at 90° for 30 minutes with 1.60 g of N-chlorosuccinimide. The solution is poured into water and extracted with chloroform. The chloroform extracts are washed several times with water, dried over magnesium sulphate and evaporated. By chromatography on a silica gel column and subsequent recrystallization from ethyl acetate there is obtained (S)-1,7-dichloro-11,12,13,13a-tetrahydro-9H-imidazo[1,5-a]pyrrolo[2,1-c][1,4]benzodiazepin-9-one of melting point 209°–210°.

EXAMPLE 20

(a) A solution of 21.6 g (0.10 mol) of (S)-(+)-1,2,3,11a-tetrahydro-5H-pyrrolo[2,1-c][1,4]benzodiazepine-5,11(10)-dione in 100 ml of dry dimethylformamide is treated under an argon atmosphere with 13.5 g (0.12 mol) of potassium t-butylate, the temperature rising from 24° to 46°. The mixture is cooled to room temperature and 18.2 g (0.105 mol) of diethylchlorophosphate are added dropwise thereto at a temperature between 18° and 23°.

Separately, 11.2 g (0.10 mol) of potassium t-butylate are dissolved in 30 ml of dimethylformamide. This solution is cooled to about −50° and treated under argon with 11.3 g (0.10 mol) of ethyl isocyanoacetate. Subsequently, this solution is added dropwise at 18° to 23° while cooling to the mixture obtained according to the preceding paragraph. The mixture is stirred at room temperature for 1 hour, 5 ml of acetic acid are added thereto, then the mixture is poured into 500 ml of water and extracted twice with 200 ml of chloroform each time. The combined chloroform phases are washed three times with 300 ml of water each time, dried over magnesium sulphate and evaporated. 150 ml of acetic acid are added to the oily residue and it is left to crystallize at 0°. The separated crystals are filtered off under suction and washed with cold ethyl acetate to give ethyl (S)-11,12,13,13a-tetrahydro-9-oxo-9H-imidazo[1,5-a]pyrrolo[2,1-c][1,4]benzodiazepine-1-carboxylate of melting point 196°–197°. The mother liquor is evaporated and the residue is dissolved in 50 ml of ethyl acetate. A further portion of the desired product of melting point 195°–196° crystallizes from the solution.

(b) A solution of 12.45 g (0.04 mol) of ethyl (S)-11,12,13,13a-tetrahydro-9-oxo-9H-imidazo[1,5-a]pyrrolo[2,1-c][1,4]benzodiazepine-1-carboxylate and 1.6 g (0.04 mol) of sodium hydroxide in 100 ml of ethanol and 25 ml of water is heated to boiling under reflux for 30 minutes. Subsequently, 40 ml of 1 N hydrochloric acid are added thereto and the mixture is evaporated to half of the volume. The crystals which thereby precipitate are filtered off under suction, washed with water and dried. There is obtained (S)-11,12,13,13a-tetrahydro-9-oxo-9H-imidazo[1,5-a]pyrrolo[2,1-c][1,4]benzodiazepine-1-carboxylic acid of decomposition point 225°.

(c) 8.8 g of (S)-11,12,13,13a-tetrahydro-9-oxo-9H-imidazo[1,5-a]pyrrolo[2,1-c][1,4]benzodiazepine-1-carboxylic acid are heated to 240°. After completion of the carbon dioxide evolution, the residue is recrystallized from ethyl acetate. There is obtained (S)-11,12,13,13a-tetrahydro-9H-imidazo[1,5-a]pyrrolo[2,1-c][1,4]benzodiazepin-9-one of melting point 211°–212°.

EXAMPLE 21

2.5 g (10.4 mmol) of (S)-11,12,13,13a-tetrahydro-9H-imidazo[1,5-a]pyrrolo[2,1-c][1,4]benzodiazepin-9-one in 20 ml of dimethylformamide are stirred at room temperature for 1 hour and at 75° for 20 minutes with 1.40 g (10.4 mmol) of N-chlorosuccinimide. The solution is poured into water and extracted with chloroform. The chloroform extracts are washed several times with water, dried over magnesium sulphate and evaporated. By chromatography of the residue on a silica gel column there is obtained (S)-1-chloro-11,12,13,13a-tetrahydro-9H-imidazo[1,5-a]pyrrolo[2,1-c][1,4]benzodiazepin-9-one of melting point 233°–234.5°.

EXAMPLE 22

2.5 g (10.4 mmol) of (S)-11,12,13,13a-tetrahydro-9H-imidazo[1,5-a]pyrrolo[2,1-c][1,4]benzodiazepin-9-one in 20 ml of dimethylformamide are stirred at room temperature for 30 minutes with 1.86 g (10.4 mmol) of N-bromosuccinimide. The solution is poured into water and extracted with chloroform. The chloroform extracts are washed several times with water, dried over magnesium sulphate and evaporated. After two-fold recrystallization from ethyl acetate, there is obtained (S)-1-bromo-11,12,13,13a-tetrahydro-9H-imidazo[1,5- a]pyrrolo[2,1-c][1,4]benzodiazepin-9-one of melting point 225°–226°.

EXAMPLE 23

A mixture of 1.1 g (4.5 mmol) of 4,5-dihydro-3-(hydroxymethyl)-5-methyl-6H-imidazo[1,5-a][1,4]benzodiazepin-6-one, 0.3 ml (5.0 mmol) of methyl iodide and 10 ml of dry dimethylformamide is treated with 0.2 g (4.5 mmol) of sodium hydride (55 percent oil dispersion, washed with n-hexane) and the mixture is stirred at room temperature for about 16 hours. The mixture is poured into 70 ml of water and extracted three times with chloroform. The chloroform solution is washed once with water, dried over magnesium sulphate and evaporated. The crude product is chromatographed on silica gel while eluting with chloroform containing 5% of methanol. Recrystallization of the material obtained from ethyl acetate/hexane yields 4,5-dihydro-3-(methoxymethyl)-5-methyl-6H-imidazo[1,5-a][1,4]benzodiazepin-6-one of melting point 115°–116°.

EXAMPLE 24

(a) A solution of 0.39 g (17.9 mmol) of lithium borohydride in 40 ml of dry tetrahydrofuran is added dropwise to a hot solution of 5.2 g (16.2 mmol) of ethyl 7-chloro-5,6-dihydro-5-methyl-6-oxo-4H-imidazo[1,5-a][1,4]benzodiazepine-3-carboxylate in 180 ml of dry tetrahydrofuran. The mixture is stirred at the boiling point for 4 hours and subsequently treated dropwise at room temperature with 10.4 ml of 3 N hydrochloric acid. The mixture obtained is heated to boiling under reflux for 1.5 hours. The tetrahydrofuran is removed in vacuo, the aqueous residue is treated with concentrated ammonia until the mixture is basic and extracted three times with methylene chloride. The methylene chloride solution is dried over magnesium sulphate and evaporated in vacuo. After recrystallization from ethanol, the crystalline residue yields 7-chloro-4,5-dihydro-3-(hydroxymethyl)-5-methyl-6H-imidazo[1,5-a][1,4]benzodiazepin-6-one of melting point 207°–208°.

(b) A mixture of 2.22 g (8 mmol) of 7-chloro-4,5-dihydro-3-(hydroxymethyl)-5-methyl-6H-imidazo[1,5-a][1,4]benzodiazepin-6-one, 0.6 ml (10 mmoL) of methyl iodide and 20 ml of dry dimethylformamide is treated with 0.4 g (9 mmol) of sodium hydride (55 percent oil dispersion, washed with n-hexane) and the mixture is stirred at room temperature for 23 hours. The mixture is poured into 50 ml of water and extracted four times with methylene chloride. The methylene chloride solution is dried over magnesium sulphate and evaporated. The crude product is chromatographed on silica gel using methylene chloride containing 1% of methanol for the elution. By subsequent recrystallization from ethyl acetate/n-hexane there is obtained 7-chloro-4,5-dihydro-3-(methoxymethyl)-5-methyl-6H-imidazo[1,5-a][1,4]benzodiazepin-6-one of melting point 143°–144°.

3,7-Dichloro-4,5-dihydro-5-methyl-6H-imidazo[1,5-a][1,4]benzodiazepin-6-one (active substance A), (R,S)-1,8-dichloro-11,13a-dihydro-9H-imidazo[1,5-a]pyrrolo[2,1-c][1,4]benzodiazepin-9-one (active substance B) and 3-chloro-4,5-dihydro-5-methyl-6H-imidazo[1,5-a][1,4]benzodiazepin-6-one (active substance C) can be used as the active substance for the pharmaceutical preparations as illustrated in Examples A to G:

EXAMPLE A

Tablets containing the following ingredients are manufactured in the usual manner:

|  | mg/tablet |
| --- | --- |
| Active substance A, B or C | 1 |
| Lactose | 103 |
| Maize starch | 25 |
| Microcrystalline cellulose | 70 |
| Magnesium stearate | 1 |
| Total | 200 |

EXAMPLE B

Capsules containing the following ingredients are manufactured:

|  | mg/capsule |
| --- | --- |
| Active substance A, B or C | 1 |
| Lactose | 164 |
| Maize starch | 30 |
| Talc | 5 |
| Total | 200 |

The active substance, the lactose and the maize starch are firstly mixed in a mixer and then in a comminuting machine. The mixture is returned to the mixer, the talc is added thereto and mixed thoroughly. The mixture is filled by machine into hard gelatine capsules.

EXAMPLE C

Injection solutions containing the following ingredients are manufactured:

|  | Per ml |
| --- | --- |
| Active substance A, B or C | 0.5 mg |
| Benzyl alcohol | 0.015 ml |
| Propyleneglycol | 0.4 ml |
| Ethanol (95 percent) | 0.1 ml |
| Sodium benzoate | 48.8 mg |
| Benzoic acid | 1.2 mg |
| Water for injection q.s. ad | 1.0 ml |

For the manufacture of 10,000 ml of injection solution, 5 g of the active substance are dissolved in 150 ml of benzyl alcohol and 4000 ml of propyleneglycol and 1000 ml of ethanol are added thereto. Then, 12 g of benzoic acid are dissolved in the above mixture and there is added thereto a solution of 488 g of sodium benzoate in 300 ml of water for injection. The solution obtained is made up to a volume of 10,000 ml, filtered and filled into ampoules of suitable size; the residual volume of the ampoules is filled with nitrogen, the ampoules are sealed and sterilized for 30 minutes in an autoclave at 0.7 atmosphere.

EXAMPLE D

Suppositories containing the following ingredients are manufactured:

|  | g/suppository |
| --- | --- |
| Active substance A, B or C | 0.001 |
| Cocoa butter (m.p. 36–37°) | 1.255 |
| Carnauba wax | 0.044 |
| Total | 1.3 |

The cocoa butter and carnauba wax are melted in a glass or steel vessel, mixed thoroughly and cooled to 45°. Thereupon, there is added thereto the finely powdered active substance and the mixture is stirred until it is completely dispersed. The mixture is poured into suppository moulds of suitable size, left to cool, the suppositories are then removed from the moulds and packed individually in wax paper or metal foil.

EXAMPLE E

Capsules containing the following ingredients are manufactured:

|  | mg/capsule |
| --- | --- |
| Active substance A, B or C (+)-5-(o-Chlorophenyl)-1,3-dihydro-3-methyl-7-nitro-2H-1,4-benzodiazepin-2-one (active substance D) | 20.0 |
|  | 30.0 |
| Lactose (crystalline) | 100.0 |
| Maize starch (white) | 27.5 |
| Talc | 10.0 |
| Magnesium stearate | 2.5 |
| Total | 190.0 |

The two active substances are mixed well with the adjuvants and 190.0 mg of the mixture are filled into interlocking capsules of suitable size.

EXAMPLE F

Tablets containing the following ingredients are manufactured:

|  | mg/tablet |
| --- | --- |
| Active substance A, B or C (+)-5-(o-Chlorophenyl)-1,3-dihydro-3-methyl-7-nitro-2H-1,4-benzodiazepin-2-one (active substance D) | 10.0 |
|  | 30.0 |
| Lactose (powdered) | 15.0 |
| Maize starch (white) | 19.5 |
| Povidon K30 | 3.5 |
| Maize starch (white) | 10.0 |
| Magnesium stearate | 2.0 |
| Total | 90.0 |

The two active substances, the powdered lactose and the first portion of white maize starch are mixed and sieved. This mixture is moistened with a solution of the Povidon K30 in water, kneaded, granulated, dried and sieved. The second portion of white maize starch and the magnesium stearate are added to the granulate. After mixing, the mass obtained is pressed to tablets weighing 90 mg.

EXAMPLE G

Tablets containing the following ingredients are manufactured:

|  | mg/tablet |
| --- | --- |
| Active substance A, B or C (+)-5-(o-Chlorophenyl)-1,3-dihydro-3-methyl-7-nitro-2H-1,4-benzodiazepin-2-one (active substance D) | 30 |
|  | 30 |
| Lactose (powdered) | 22 |
| Maize starch (white) | 22 |
| Povidon K30 | 6 |
| Maize starch (white) | 16 |
| Magnesium stearate | 4 |
| Total | 130 |

The two active substances, the powdered lactose and the first portion of white maize starch are mixed and sieved. This mixture is moistened with a solution of the Povidon K30 in water, kneaded, granulated, dried and sieved. The second portion of white maize starch and the magnesium stearate are added to the granulate. After mixing, the mass obtained is pressed to tablets weighing 130 mg.

What is claimed:

1. A compound of the formula

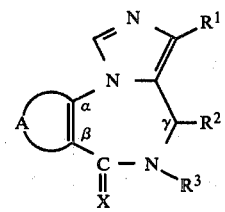

wherein A together with the two carbon atoms denoted as α and β is the group

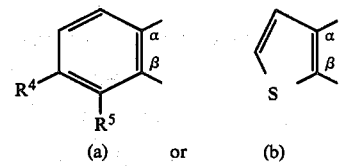

(a)    or    (b)

$R^1$ is hydrogen, lower alkyl, lower alkoxymethyl, halogen or nitro, $R^4$ is hydrogen, trifluoromethyl or halogen, $R^5$ is hydrogen, trifluoromethyl, halogen or lower alkyl and X is an oxygen or sulphur atom, and either $R^2$ is hydrogen and $R^3$ is lower alkyl or $R^2$ and $R^3$ together are trimethylene or propylene and the carbon atom denoted as γ has the (S)— or (R,S)— configuration, and pharmaceutically acceptable acid addition salts thereof.

2. The compound of claim 1, wherein $R^1$ is hydrogen, methyl, methoxymethyl, halogen or nitro.

3. The compound of claim 2, wherein $R^3$ is methyl when $R^2$ is hydrogen.

4. The compound of claim 2, wherein the carbon atom denoted as γ in formula I has the (S)-configuration when $R^2$ and $R^3$ together are trimethylene.

5. The compound of claim 4, wherein $R^4$ is hydrogen, chlorine or fluorine and $R^5$ is hydrogen or chlorine, whereby at least one of $R^4$ and $R^5$ is hydrogen, when A together with the two carbon atoms denoted as α and β is group (a).

6. The compound: 3,7-Dichloro-4,5-dihydro-5-methyl-6H-imidazo[1,5-a][1,4]benzodiazepin-6-one.

7. The compound: (R,S)-1,8-Dichloro-11,13a-dihydro-9H-imidazo[1,5-a]pyrrolo[2,1-c][1,4]benzodiazepin-9-one.

8. The compound: 3-Chloro-4,5-dihydro-5-methyl-6H-imidazo[1,5-a][1,4]benzodiazepin-6-one.

9. The compound: 7-Chloro-4,5-dihydro-3-(methoxymethyl)-5-methyl-6H-imidazo[1,5-a][1,4]benzodiazepin-6-one.

10. A compound selected from the group consisting of (S)-1-Chloro-10,11,12,12a-tetrahydro-8H-imidazo[5,1-c]pyrrolo[1,2-a]thieno[3,2-e][1,4]diazepin-8-one, 3-chloro-8-fluoro-4,5-dihydro-5-methyl-6H- imidazo[1,5-a][1,4]benzodiazepin-6-one, 4,5-dihydro-3-(methoxymethyl)-5-methyl-6H-imidazo[1,5-a][1,4]benzodiazepin-6-one, 4,5-dihydro-3-iodo-5-methyl-6H-imidazo[1,5-a][1,4]benzodiazepin-6-one, 4,5-dihydro-5-methyl-3-nitro-6H-imidazo[1,5-a][1,4]benzodiazepin-6-one, 3-bromo-4,5-dihydro-5-methyl-6H-imidazo[1,5-a][1,4]benzodiazepin-6-one, 7-chloro-4,5-dihydro-5-methyl-6H-imidazo[1,5-a][1,4]benzodiazepin-6-one, 3-bromo-8-fluoro-4,5-dihydro-5-methyl-6H-imidazo[1,5-a][1,4]benzodiazepin-6-one, 3-chloro-4,5-dihydro-5-methyl-6H-imidazo[1,5-a][1,4]benzodiazepine-6-thione, (S)-1-chloro-11,12,13,13a-tetrahydro-9H-imidazo[1,5-a]pyrrolo[2,1-c][1,4]benzodiazepin-9-one, (S)-1-bromo-11,12,13,13a-tetrahydro-9H-imidazo[1,5-a]pyrrolo[2,1-c][1,4]benzodiazepin-9-one or (R,S)-8-chloro-11,13a-dihydro-9-H-imidazo[1,5-a]pyrrolo[2,1-c][1,4]benzodiazepin-9-one.

11. A method of antagonising, in a patient, the central-depressant, muscle relaxant, ataxic, blood pressure-lowering and respiratory-depressant properties of 1,4-benzodiazepines which have tranquillizing activity which comprises the administration to said patient of from about 0.2 mg to about 500 mg daily of a compound of the formula

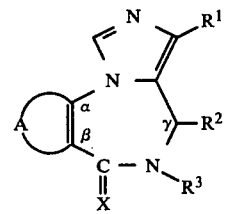

where A together with the two carbon atoms denoted as α and β is the group

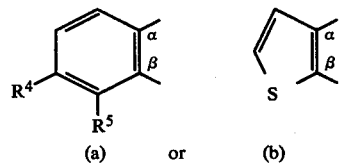

$R^1$ is hydrogen, lower alkyl, lower alkoxymethyl, halogen or nitro, $R^4$ is hydrogen, trifluoromethyl or halogen, $R^5$ is hydrogen, trifluoromethyl, halogen or lower alkyl and X is an oxygen or sulphur atom and either $R^2$ is hydrogen and $R^3$ is lower alkyl or $R^2$ and $R^3$ together are trimethylene or propenylene and the carbon atom denoted as γ has the (S)— or (R,S)—configuration.

and the pharmaceutically acceptable acid addition salts thereof.

12. The method of claim 11 wherein the 1,4-benzodiazepine exhibits activity in the control of schistosomiasis.

* * * * *